(12) United States Patent
Delucia (10) Patent No.: US 8,786,210 B2
(45) Date of Patent: Jul. 22, 2014

(54) DRIVE CIRCUIT FOR LIGHT EMITTING DIODE

(75) Inventor: Paul Delucia, Baldwinsville, NY (US)

(73) Assignee: Welch Allyn, Inc., Skaneateles Falls, NY (US)

(*) Notice: Subject to any disclaimer, the term of this patent is extended or adjusted under 35 U.S.C. 154(b) by 551 days.

(21) Appl. No.: 12/827,688

(22) Filed: Jun. 30, 2010

(65) Prior Publication Data

US 2012/0004509 A1    Jan. 5, 2012

(51) Int. Cl.
*H05B 37/02*    (2006.01)

(52) U.S. Cl.
USPC ............ 315/297; 315/200; 315/291; 315/246; 315/185 R; 315/307

(58) Field of Classification Search
USPC ......................................... 315/287, 297, 291
See application file for complete search history.

(56) References Cited

U.S. PATENT DOCUMENTS

| | | | |
|---|---|---|---|
| 1,556,914 A | 10/1925 | Clement et al. |
| 1,648,013 A | 11/1927 | Copeland |
| 1,774,832 A | 9/1930 | Keeler |
| 1,795,691 A | 3/1931 | Wilson |
| 1,804,151 A | 5/1931 | Copeland |
| 1,828,777 A | 10/1931 | Leventhal |
| 1,927,111 A | 9/1933 | Carpenter |
| 1,944,406 A | 1/1934 | Crofton |
| 2,027,663 A | 1/1936 | Allyn |
| 2,204,014 A | 6/1940 | Grout |
| 2,214,802 A | 9/1940 | Tillyer |
| 2,331,591 A | 10/1943 | Arnesen |
| 2,448,140 A | 8/1948 | Bonaventura |
| 2,501,438 A | 3/1950 | Copeland |
| 2,715,352 A | 8/1955 | Jobe |
| 2,882,789 A | 4/1959 | Wilson |

(Continued)

FOREIGN PATENT DOCUMENTS

| | | |
|---|---|---|
| FR | 2773701 A1 | 7/1999 |
| GB | 1244529 A | 9/1971 |

(Continued)

OTHER PUBLICATIONS

Nishikawa et al, An LED Drive Circuit with Constant-Output-Circuit and Constant-Luminance Control, Telecommunications Energy Conference, 2006 28th Annual International ( 1-4244-0430-4) 2006 p. 1-6.*

(Continued)

*Primary Examiner* — Douglas W Owens
*Assistant Examiner* — Srinivas Sathiraju
(74) *Attorney, Agent, or Firm* — Merchant & Gould P.C.

(57) ABSTRACT

A drive circuit for a light emitting diode, and applications thereof, are disclosed. In one example, the drive circuit includes an input voltage and a ground, and a current control block including a voltage supply connection, a ground connection, a first voltage sense connection, and a second voltage sense connection. The voltage supply connection electrically connects to the input voltage and the ground connection connected to the ground. The drive circuit includes a current sense resistor connected to the first voltage sense connection, a first current adjustment resistor connected between the current sense resistor and the second voltage sense connection, and a second current adjustment resistor connected between the second voltage sense connection and the input voltage. A light emitting diode can connect from a point between the current sense resistor and the first current adjustment resistor to the ground.

22 Claims, 7 Drawing Sheets

(56) References Cited

U.S. PATENT DOCUMENTS

| | | |
|---|---|---|
| 3,439,978 A | 4/1969 | Moore et al. |
| 3,597,051 A | 8/1971 | Copeland et al. |
| 3,600,098 A | 8/1971 | Mohrman |
| 3,708,230 A | 1/1973 | Terranova |
| 3,715,166 A | 2/1973 | Leighty et al. |
| 3,724,931 A | 4/1973 | Nevyas et al. |
| 3,812,847 A | 5/1974 | Moore et al. |
| 3,832,041 A | 8/1974 | Lieberman |
| 3,978,850 A | 9/1976 | Moore et al. |
| D243,973 S | 4/1977 | Pulos et al. |
| 4,234,910 A | 11/1980 | Price |
| 4,251,139 A | 2/1981 | Matsumura |
| 4,257,688 A | 3/1981 | Matsumura |
| 4,326,529 A | 4/1982 | Doss et al. |
| 4,395,097 A | 7/1983 | Mohrman |
| 4,396,258 A | 8/1983 | Hazard |
| 4,407,571 A | 10/1983 | Augusto et al. |
| 4,426,140 A | 1/1984 | Stephens |
| 4,464,608 A | 8/1984 | Pilley |
| 4,482,844 A * | 11/1984 | Schweer et al. ............. 315/194 |
| 4,496,225 A | 1/1985 | Augusto |
| 4,496,226 A | 1/1985 | Augusto et al. |
| 4,500,180 A | 2/1985 | Stevens |
| 4,514,476 A | 4/1985 | Fitzgerald |
| 4,526,449 A | 7/1985 | Newman et al. |
| 4,527,552 A | 7/1985 | Hattori |
| 4,537,480 A | 8/1985 | Akaba et al. |
| 4,576,454 A | 3/1986 | Charney et al. |
| 4,643,546 A | 2/1987 | Richards |
| 4,699,482 A | 10/1987 | Utsugi |
| 4,710,002 A | 12/1987 | Pomerantzeff |
| 4,758,080 A | 7/1988 | Howland |
| 4,778,268 A | 10/1988 | Randle |
| 4,834,528 A | 5/1989 | Howland et al. |
| 4,854,302 A | 8/1989 | Allred, III |
| 4,979,812 A | 12/1990 | Reese |
| 4,991,069 A | 2/1991 | Tiller |
| 4,998,818 A | 3/1991 | Kugler et al. |
| 4,998,820 A | 3/1991 | Salibello et al. |
| 5,144,190 A | 9/1992 | Thomas et al. |
| 5,144,495 A | 9/1992 | Merton et al. |
| 5,189,449 A | 2/1993 | Perkins |
| 5,191,367 A | 3/1993 | Salibello et al. |
| 5,200,772 A | 4/1993 | Perkins et al. |
| 5,202,710 A | 4/1993 | Perkins |
| 5,325,136 A | 6/1994 | Salibello et al. |
| 5,394,201 A | 2/1995 | Hauptli |
| 5,419,312 A | 5/1995 | Arenberg et al. |
| 5,429,119 A | 7/1995 | Griffin et al. |
| 5,430,508 A | 7/1995 | Sims |
| 5,430,509 A | 7/1995 | Kobayashi |
| 5,440,360 A | 8/1995 | Torrey et al. |
| 5,450,144 A | 9/1995 | Ben Nun |
| 5,459,535 A | 10/1995 | Cleveland et al. |
| 5,500,698 A | 3/1996 | Sims |
| 5,512,966 A | 4/1996 | Snook |
| 5,515,118 A | 5/1996 | Torrey et al. |
| 5,520,363 A | 5/1996 | Burton et al. |
| 5,528,323 A | 6/1996 | Fujieda et al. |
| 5,559,422 A | 9/1996 | Fahrenkrug et al. |
| 5,568,208 A | 10/1996 | Van de Velde |
| 5,568,209 A | 10/1996 | Priester et al. |
| 5,580,023 A | 12/1996 | Burton et al. |
| 5,594,826 A | 1/1997 | Wood et al. |
| 5,599,276 A | 2/1997 | Hauptli et al. |
| 5,614,966 A | 3/1997 | Iijima et al. |
| D379,514 S | 5/1997 | Laun et al. |
| 5,650,839 A | 7/1997 | Sims |
| 5,734,459 A | 3/1998 | Chang |
| 5,757,460 A | 5/1998 | Cockley |
| 5,838,421 A | 11/1998 | Pedack |
| 5,841,509 A | 11/1998 | Harooni et al. |
| 5,859,687 A | 1/1999 | Heine et al. |
| 5,861,939 A | 1/1999 | Heacock |
| 5,885,214 A | 3/1999 | Monroe et al. |
| 5,886,770 A | 3/1999 | Damato |
| 5,887,965 A | 3/1999 | Edens et al. |
| 5,892,569 A | 4/1999 | Van de Velde |
| 5,919,130 A | 7/1999 | Monroe et al. |
| 5,943,117 A | 8/1999 | Van de Velde |
| 6,003,993 A | 12/1999 | Webb |
| 6,079,830 A | 6/2000 | Kohayakawa |
| 6,142,629 A | 11/2000 | Adel et al. |
| 6,158,863 A | 12/2000 | Afran |
| 6,250,761 B1 | 6/2001 | Little et al. |
| 6,318,887 B1 | 11/2001 | Matsumoto |
| 6,340,868 B1 | 1/2002 | Lys et al. |
| 6,361,167 B1 | 3/2002 | Su et al. |
| 6,368,270 B1 | 4/2002 | Takami |
| 6,370,003 B1 | 4/2002 | Hennick |
| 6,390,625 B1 | 5/2002 | Slawson et al. |
| 6,406,437 B1 | 6/2002 | Zur et al. |
| 6,439,715 B2 | 8/2002 | Burckhardt |
| 6,447,119 B1 | 9/2002 | Stewart et al. |
| 6,454,412 B1 | 9/2002 | Torrey |
| 6,459,919 B1 | 10/2002 | Lys et al. |
| 6,513,931 B1 | 2/2003 | Torrey et al. |
| 6,520,640 B1 | 2/2003 | Binnun |
| 6,527,390 B2 | 3/2003 | Goldfain et al. |
| 6,550,917 B1 | 4/2003 | Neal et al. |
| 6,572,230 B2 | 6/2003 | Levine |
| 6,582,079 B2 | 6/2003 | Levine |
| 6,595,643 B2 | 7/2003 | Levine |
| 6,609,794 B2 | 8/2003 | Levine |
| 6,611,320 B1 | 8/2003 | Lindberg et al. |
| 6,631,991 B2 | 10/2003 | Wirth |
| 6,637,882 B1 | 10/2003 | Goldfain et al. |
| 6,652,100 B1 | 11/2003 | Little et al. |
| 6,669,341 B2 | 12/2003 | Wirth |
| 6,688,745 B2 | 2/2004 | Ross et al. |
| 6,709,108 B2 | 3/2004 | Levine et al. |
| 6,726,327 B2 | 4/2004 | Torrey et al. |
| 6,766,042 B2 | 7/2004 | Freeman et al. |
| 6,789,900 B2 | 9/2004 | Van de Velde |
| 6,830,347 B2 | 12/2004 | Slawson et al. |
| 6,869,182 B2 | 3/2005 | Tajiri |
| 6,939,006 B2 | 9/2005 | Goldfain et al. |
| 6,964,480 B2 | 11/2005 | Levine |
| 7,040,776 B2 | 5/2006 | Harrell et al. |
| 7,276,025 B2 | 10/2007 | Roberts et al. |
| 7,311,401 B2 | 12/2007 | Goldfain et al. |
| 7,350,920 B2 | 4/2008 | Levine |
| 7,364,297 B2 | 4/2008 | Goldfain et al. |
| 7,427,135 B2 | 9/2008 | Chen et al. |
| 7,448,752 B2 | 11/2008 | Levine |
| 7,458,934 B2 | 12/2008 | Roberts et al. |
| 7,533,992 B2 | 5/2009 | Williams |
| 7,553,020 B2 | 6/2009 | Goldfain et al. |
| 7,556,378 B1 | 7/2009 | Ianchulev |
| 7,607,776 B1 | 10/2009 | Lewis et al. |
| 7,683,365 B2 | 3/2010 | Nii |
| 7,731,364 B2 | 6/2010 | Peyman |
| 7,764,028 B2 * | 7/2010 | Mariyama et al. ............ 315/360 |
| 7,766,478 B2 | 8/2010 | Phillips |
| 7,772,786 B2 * | 8/2010 | Hosoda et al. ................ 315/291 |
| 7,784,940 B2 | 8/2010 | Goldfain et al. |
| 8,111,014 B2 * | 2/2012 | Van Erp et al. ................ 315/307 |
| 8,400,081 B2 * | 3/2013 | Catalano et al. .............. 315/309 |
| 2010/0026209 A1 * | 2/2010 | Liu ................................ 315/297 |
| 2010/0039456 A1 * | 2/2010 | Um et al. ....................... 345/694 |
| 2010/0052572 A1 * | 3/2010 | Kataoka et al. ................ 315/297 |
| 2010/0164404 A1 * | 7/2010 | Shao et al. ..................... 315/297 |
| 2010/0314986 A1 | 12/2010 | Gershaw |
| 2011/0054263 A1 | 3/2011 | Chou et al. |
| 2011/0080112 A1 * | 4/2011 | Shearer et al. ................ 315/291 |

FOREIGN PATENT DOCUMENTS

| | | |
|---|---|---|
| GB | 1372646 | 11/1974 |
| GB | 2310051 A | 8/1997 |
| JP | 2002134284 A | 5/2002 |
| JP | 2008077862 A | 4/2008 |
| KR | 1020070113681 A | 11/2007 |
| KR | 1020090075487 A | 7/2009 |

(56) References Cited

FOREIGN PATENT DOCUMENTS

| WO | WO 89/08475 | | 9/1989 | | |
|----|----|----|----|----|----|
| WO | WO 98/49931 | A1 | 11/1998 | | |
| WO | WO 01/60241 | A1 | 8/2001 | | |
| WO | WO 2008135737 | A1 * | 11/2008 | ............... | A61B 1/31 |

OTHER PUBLICATIONS

M Nishikawa et al "An LED drive circuit with constant output current control and constant Luminance Control" 8-2, 2006.*

M Nishikawa et al An LED drive circuit with constant current output-current control and constant-Luminance Control IEEE transaction 2006.*

International Search Report and Written Opinion in PCT/US2011/037292 mailed Dec. 15, 2011, 8 pages.

Dreher, Andreas W.: Field Portable Digital Ophthalmoscope/Fundus Camera—Final Report Nov. 6, 1996-May 5, 1997; Jun. 1997; published by Laser Diagnostic Technologies, Inc.; 26 pgs.

Kondo et al.: Recording Multifocal Electroretinograms with Fundus Monitoring; vol. 38 No. 5; Apr. 1997; published by Investigative Ophthalmology & Visual Science; pp. 1049-1052.

Neurosurgery: A Manual and Atlas of Medical Ophthalmoscopy; vol. 36(5), May 1995, Copyright © by the Library of Congress of Neurological Surgeons, pp. 1052-1056.

Schaeffel et al.: Lower-field Myopia and Astigmatism in Amphibians and Chickens; JOSA A, vol. 11, Issue 2, Feb. 1994; pp. 487-495.

Welch Allyn: Diagnostic Instruments (Product literature/brochure); 1984, SL 1540; 27 pgs.

Welch Allyn: Electrically Illuminated Diagnostic Instruments, Mar. 15, 1966; 17 pgs.

Blair, Frank W.: Activities of the Chihuahua Deer-Mouse in Relation to Light Intensity; Journal of Wildlife Management; vol. 7; No. 1; Jan. 1943; pp. 92-97.

Colvard, M: Abstract of—Preoperative Measurement of Scotopic Pupil Dilation Using an Office Pupillometer; Center for Ophthalmic Surgery; Journal of Cataract and Refractive Surgery; 1998; vol. 24, No. 12; pp. 1594-1597.

Ferree, C.E. et al.: Intensity of Light in Relation to the Examination of the Eye; The British Journal of Ophthalmology; 1936; pp. 331-346.

Heimel, J et al.: SNOM/STM Using a Tetrahedral Tip and a Sensitive Current-to-Voltage Converter; Journal of Microscopy, vol. 202, Pt. I; Apr. 2001; pp. 53-59.

Talbot, S.A. et al.: A Multibeam Ophthalmoscope for the Study of Retinal Physiology; Journal of the Optical Society of America; vol. 42, No. 12; Dec. 1952; pp. 931-936.

Linear Technology: "LT3591—White LED Driver with Integrated Schottky in 3mm×2mm DFN"; Linear Technology Corporation, Milpitas, CA, US; © 2007; 16 pages.

* cited by examiner

DRIVE CIRCUIT FOR LIGHT EMITTING DIODE

BACKGROUND

Otoscopes, ophthalmoscopes, and other types of orifice scopes are often used to view images of tissues/organs of a medical patient. In use, typically a scope is inserted into an orifice (e.g., ear, nose, mouth, etc.), and includes a digital or optical viewfinder allowing the medical caregiver to view the tissue(s) being examined. Such scopes typically include a light source configured to direct light toward the tissue(s) under examination. Such light sources typically are incandescent or halogen light sources, and allow the medical caregiver to adequately view tissues within the orifice.

To decrease costs and power consumption of the orifice scopes described above, as well as to incorporate a longer-life illumination element, modern systems are designed to include light emitting diodes (LEDs) rather than incandescent or halogen light sources. LED-based designs typically do not include sockets, because LEDs rarely require replacement. However, to incorporate LEDs into existing scopes while obtaining the full functionality of the scope, a socket and electrical connector must be redesigned. This is because of the different voltage and amperage requirements of an LED light source as compared to the typical halogen or incandescent light sources. For example, existing scopes provide a dimming function based on a slight voltage change input to a halogen bulb; however, existing LED drive circuits maintain a constant current through the LED, and use a separate control pin for dimming. Using an LED in the same circuit as a previous halogen bulb allow for the same type of dimming adjustment as would be included in a typical LED application, because existing halogen lamp sockets only include two leads (voltage and ground), lacking a separate control input that manages dimming. Additionally, LEDs cannot easily be dimmed by a change in voltage, because use of a voltage source (including a variable voltage source) to directly drive an LED could be damaging to the LED. Therefore, using existing circuit designs, LED light sources cannot readily be dimmed, and therefore are difficult to use as an interchangeable replacement to halogen or incandescent light sources in medical scopes. This problem also arises in other contexts as well, notably where a light source controlled by two pins is to be retrofitted for use with a light emitting diode, for example where an LED replaces a halogen or incandescent lamp and is to be used in the same socket/package as the replaced lamp.

For these and other reasons, improvements are desirable.

SUMMARY

In accordance with the following disclosure, the above and other issues are addressed by the following:

In a first aspect, a drive circuit for a light emitting diode is disclosed. The drive circuit includes an input voltage and a ground, as well as a current control block including a voltage supply connection, a ground connection, a first voltage sense connection, and a second voltage sense connection. The voltage supply connection electrically connects to the input voltage and the ground connection connected to the ground. The drive circuit also includes a current sense resistor connected to the first voltage sense connection, a first current adjustment resistor connected between the current sense resistor and the second voltage sense connection, and a second current adjustment resistor connected between the second voltage sense connection and the input voltage. A light emitting diode can be connected from a point between the current sense resistor and the first current adjustment resistor to the ground. By forming a voltage divider at the second voltage sense connection, the current through the light emitting diode can be controlled by the input voltage.

In a second aspect, a replacement light emitting diode package useable in an illumination device is disclosed. The package includes an input voltage and a ground, and a current control block including a voltage supply connection, a ground connection, a first voltage sense connection, and a second voltage sense connection. The voltage supply connection is electrically connected to the input voltage and the ground connection connected to the ground. The package also includes a current sense resistor connected to the first voltage sense connection, a first current adjustment resistor connected between the current sense resistor and the second voltage sense connection, and a second current adjustment resistor connected between the second voltage sense connection and the input voltage. The package also includes a light emitting diode connected from a point between the current sense resistor and the first current adjustment resistor to the ground.

In a third aspect, a medical scope is disclosed that includes a voltage source electrically connected to a socket, the socket comprising a voltage pin and a ground pin. The medical scope also includes a light emitting diode package sized to fit in the socket. The light emitting diode package includes a current control block including a voltage supply connection, a ground connection, a first voltage sense connection, and a second voltage sense connection, the voltage supply connection electrically connected to the voltage pin of the voltage source and the ground connection connected to the ground pin. The light emitting diode package also includes a current sense resistor connected to the first voltage sense connection, a first current adjustment resistor connected between the current sense resistor and the second voltage sense connection, and a second current adjustment resistor connected between the second voltage sense connection and the input voltage, The light emitting diode package further includes a light emitting diode connected from a point between the current sense resistor and the first current adjustment resistor to the ground.

In a fourth aspect, a drive circuit for a light emitting diode is disclosed that includes an input voltage and a ground, and a current control block including a voltage supply connection, a ground connection, a first voltage sense connection, and a second voltage sense connection. The voltage supply connection is electrically connected to the input voltage and the ground connection to the ground. The circuit further includes a current sense resistor connected to the first voltage sense connection, and a first current adjustment resistor connected between the current sense resistor and the second voltage sense connection. The circuit also includes a capacitor connected between the first and second voltage sense connections, the capacitor selected to provide an approximately constant voltage across the first and second voltage sense connections.

DETAILED DESCRIPTION

In general, the present disclosure relates to an LED drive circuit. The LED drive circuit provides a solution by which medical scopes or other illumination devices previously using incandescent or halogen light sources can be retrofitted with light emitting diodes (LEDs), while maintaining full functionality of the LEDs when installed, including dimming control and other features.

Figure 1:
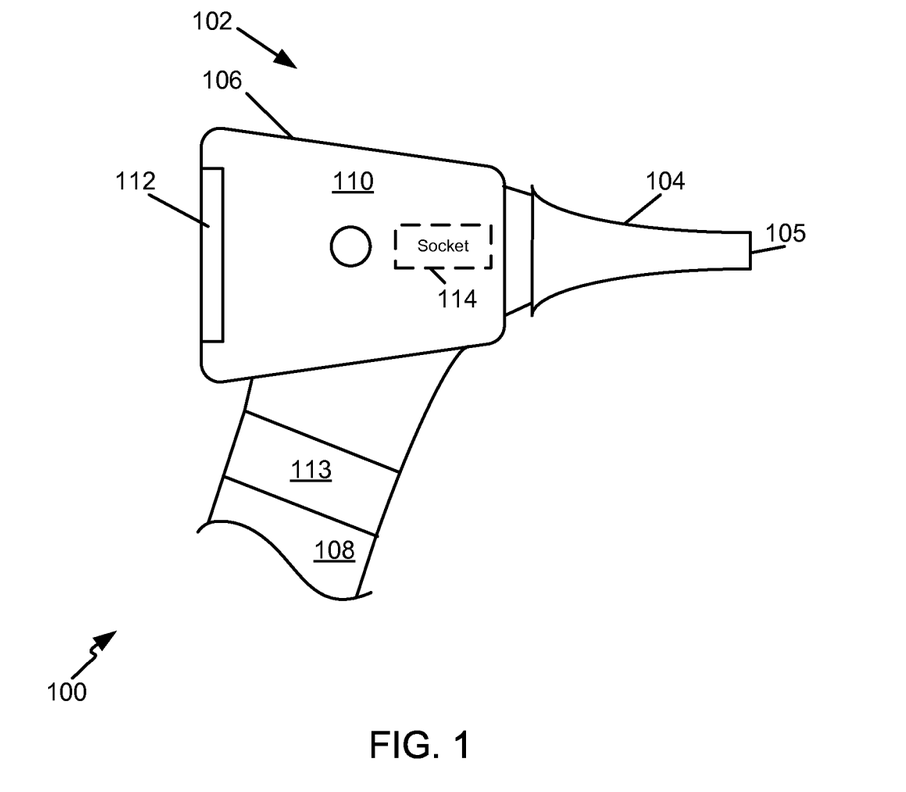
FIG. 1 illustrates an example medical scope in which the drive circuit of the present disclosure can be implemented.

FIG. 1 illustrates an example medical scope 100 in which the drive circuit of the present disclosure can be implemented. In the embodiment shown, the medical scope 100 represents an otoscope, configured to be placed in an orifice of a patient (typically the patient's ear, but possibly another orifice such as a nose or mouth). The medical scope 100 generally includes a head portion 102 that has an insertion portion 104 and a viewing portion 106. The head portion 102 can be mounted to a handle portion 108, as illustrated, for holding by a medical caregiver during examination of a patient.

In the embodiment shown, the insertion portion 104 has an opening 105 through which tissues of the orifice under examination can be viewed, and through which light from an illumination source in the medical scope 100 can be directed. The insertion portion 104 can be contoured to fit a particular orifice, or could, in different embodiments, include alternative components used as the insertion portion that are each specific to different orifices. Other arrangements are possible as well.

In the embodiment shown, the viewing portion 106 includes a scope body 110, and an optional viewfinder 112 opposite the insertion portion 104. In other embodiments, the scope body can include other components; additionally, in other embodiments, alternative types of viewfinders could be used as well. For example, in certain embodiments, a digital viewfinder would not need to include a viewfinder incorporated in the scope body 110, but can be used as a digital display remote from the scope 100. Other embodiments are possible as well.

In use, the insertion portion 108 of the scope is inserted into an orifice whose tissues are under examination. A medical caregiver can turn on a light within the scope 100 to direct light through the opening 108 to assist the caregiver in viewing the tissue by way of the viewfinder 112. The caregiver may opt to adjust a light level based on the tissue view in the viewfinder, using a dimming adjustment dial 113. As further described below, adjusting the dimming dial 113 can adjust the input voltage received at circuitry to adjust the light level.

In the embodiment shown, a socket 114 can be included in the body 110 of the medical scope 100, and can receive a replaceable lighting source. Typically, such lighting sources can include an incandescent or halogen bulb. As described below, a replacement light source package can be used as well, including a control circuit for a LED, and associated LED. This arrangement provides straightforward retrofit of the medical scope 100 with an LED light source into a system such as those receiving incandescent or halogen bulbs that use two pins for control of a lighting source.

The medical device 100 can include a number of additional components to those illustrated as well. For example a medical scope may include a battery or other power source configured to deliver power to the circuitry included therein. Other elements could be included as well.

Figure 2:
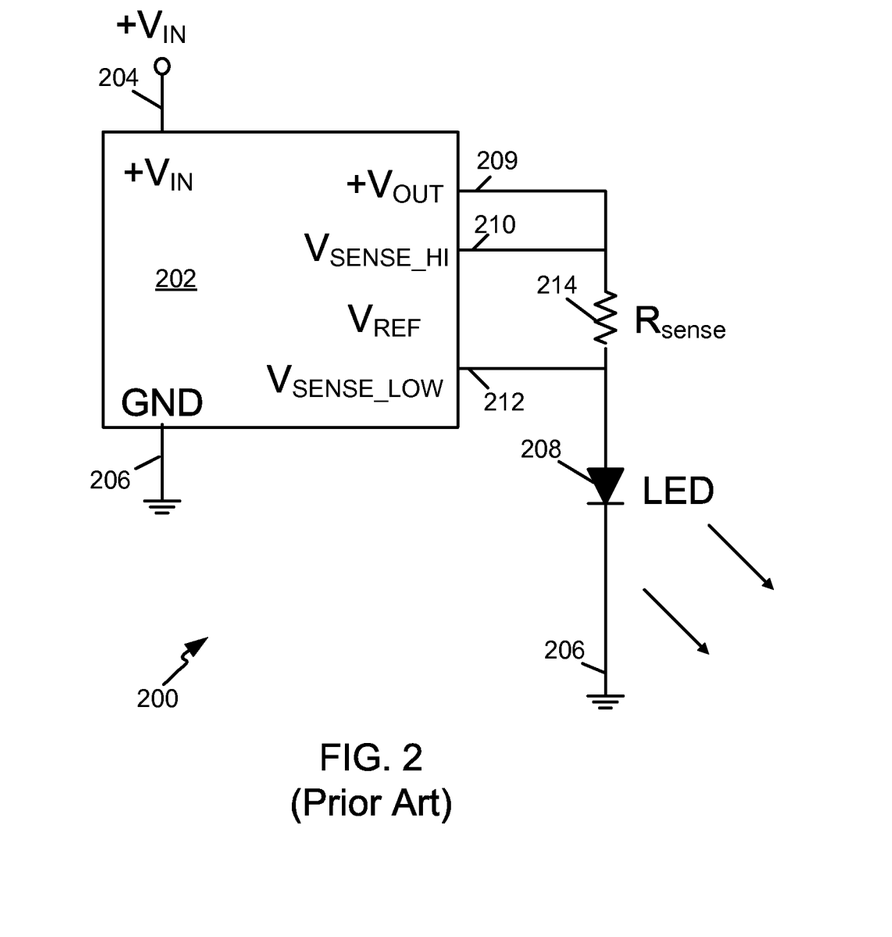
FIG. 2 illustrates a prior art LED drive circuit.

FIG. 2 illustrates a prior art LED drive circuit 200 useable to drive an LED according to certain applications. In the embodiment shown, a current controller block 202 is connected to an input voltage 204 and a ground 206. The current controller block 202 can include, in various embodiments, one or more switching or linear devices configured to provide power to a light emitting diode 208. The current controller block 202 includes an output voltage 209 as well as a first voltage sense connection 210 and a second voltage sense connection 212. The first and second voltage sense connections 210, 212 are connected across a current sense resistor 214 ($R_{sense}$), which, alongside the difference in voltage between voltage sense connections 210, 212, defines the current ($I_{led}$) across the light emitting diode 208, according to the equation:

$$I_{led} = V_{ref}/R_{sense}$$

The current controller block 202 is, in certain embodiments, designed to increase the current whenever the voltage drop across the current sense resistor (Vref) drops below a threshold voltage ($V_{ref}$). In the circuit 200, 'the voltage across the first and second voltage sense connections 210, 212 are not affected by the input voltage, and therefore would require some other control input (e.g., CTRL of FIG. 7, below).

Overall, the LED drive circuit 200 is arranged for a constant LED current application. In other words, changes to the input voltage 204 will have limited effect on the output voltage (outside of removing the input voltage entirely). This is because the output of the current controller block 202 attempts to maintain a constant reference voltage across the first and second voltage sense connections 210, 212, irrespective of input voltage. In applications where a control input is not available (e.g., retrofit applications), use of a current control input may not be possible.

Figure 3:
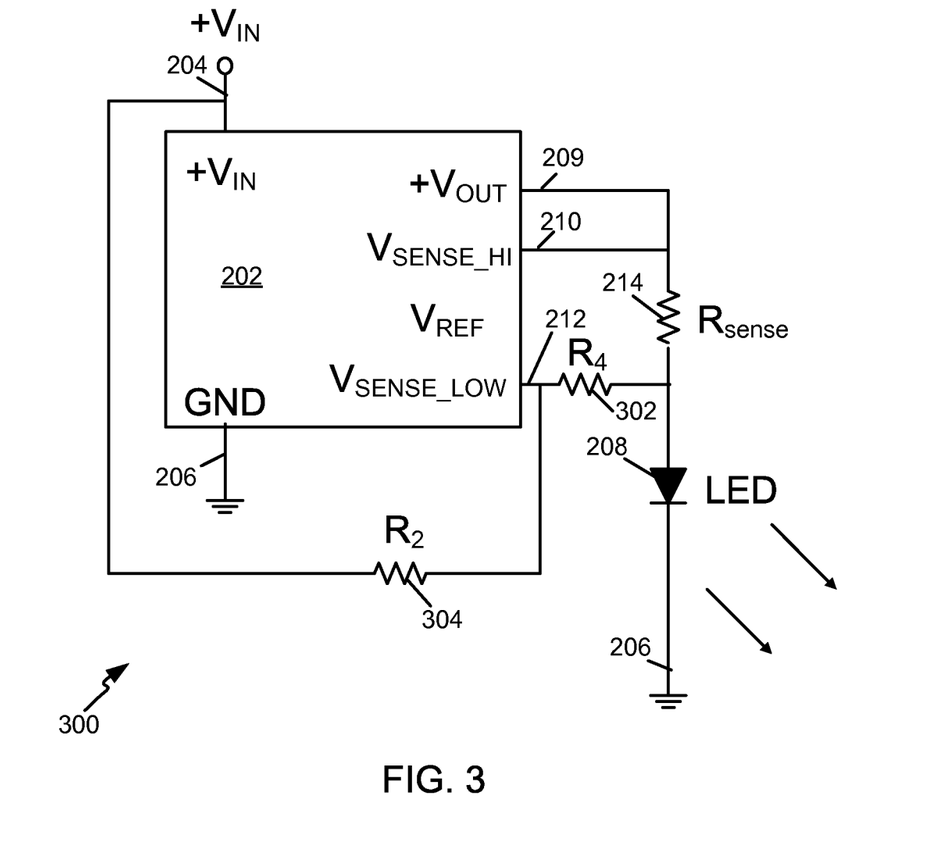
FIG. 3 is a schematic diagram of a possible LED drive circuit, according to a possible embodiment of the present disclosure.

Referring now to FIG. 3, a schematic diagram of a possible LED drive circuit 300 is shown, according to a possible embodiment of the present disclosure. As compared to circuit 200 of FIG. 2, the LED drive circuit 300 includes two additional resistors selected and configured to create a voltage divider between the input voltage 204 and the voltage at light emitting diode 208. The voltage divider is formed from a first current adjustment resistor 302 and a second current adjustment resistor 304. The first current adjustment resistor 302 (R4) is connected in between the current sense resistor 214 ($R_{sense}$) and the second voltage sense connection 212, and the second current adjustment resistor 304 (R2) is connected between the second voltage sense connection 212 and the input voltage 204. This causes the voltage at the second voltage sense connection 212 of the current controller block 202 to be affected by the difference between the input voltage and the voltage at the light emitting diode 208.

When the current controller block 202 observes an input voltage that is in fact greater than that observed at the light emitting diode 208, it causes the current controller block 202 to detect a smaller difference between voltage sense connections 210, 212, and altering the operation of the current controller block 202 accordingly. Similarly, when the current controller block 202 observes an input voltage that is in lower than that observed at the light emitting diode 208, it causes the current controller block 202 to detect a greater difference between voltage sense connections 210, 212, and altering its operation accordingly.

It is observed that the current passing through the light emitting diode 208 is at least in part represented by the voltage across the current sense resistor 214 ($R_{sense}$). The voltage difference between the first and second voltage sense connections 210, 212, modifies this current sense voltage to include the difference in voltage from the input voltage to the light emitting diode 208 ($V_{in}-V_{led}$) as follows:

$$V_{sense\_high} = V_{led} + V_{led} R_{sense}$$

$$V_{sense\_low} = V_{led} + (V_{in}-V_{led})(R4/(R2+R4))$$

Because the current controller 202 generates a current by maintaining a voltage difference $V_{ref}$ between these values ($V_{ref}=V_{sense\_high}-V_{sense\_low}$) the current at the LED corresponds to the voltage drop across the voltage sense connections 210, 212, plus the portion of the voltage difference between the input voltage 204 and the voltage at the light emitting diode 208 (as reduced by the current divider at the second voltage sense connection 212), divided by the current sense resistor:

$$I_{led} = (V_{ref} + (V_{in}-V_{led})(R4/(R2+R4)))/R_{sense}$$

This arrangement can be referred to as a "high side sense" arrangement because the current sense resistor is on the high voltage side of the light emitting diode.

It is noted that using the added resistors within the circuit 300 provides a number of advantages for using light emitting diodes within a device such as the one illustrated in FIG. 1. For example, controlling the current through the light emitting diode 208 using the input voltage allows retrofitting LEDs into existing illumination devices (e.g., medical scopes) that require a dimming capability where there is no ability to add an additional dimming control input (e.g., in the case of a halogen or incandescent lamp with only two input terminals). Additionally, the amount of gain (and resultant dimming control sensitivity) can be set by use of resistors 302, 304. This arrangement therefore provides a circuit that is sensitive to changes in input voltage, as compared to other arrangements for voltage regulation in which, for example, a resistor is connected in series with a constant power source to accomplish a dimming function.

Although the magnitudes of the resistances illustrated in FIG. 3 can vary, in certain embodiments the added current adjustment resistors 302, 304 have magnitudes greater than the current sense resistor 214. Furthermore, although in the embodiment of circuit 300 shown, only one light emitting diode 208 is illustrated, it is understood that the present disclosure contemplates use of a similar circuit in cases where additional light emitting diodes are incorporated as well.

Figure 4:
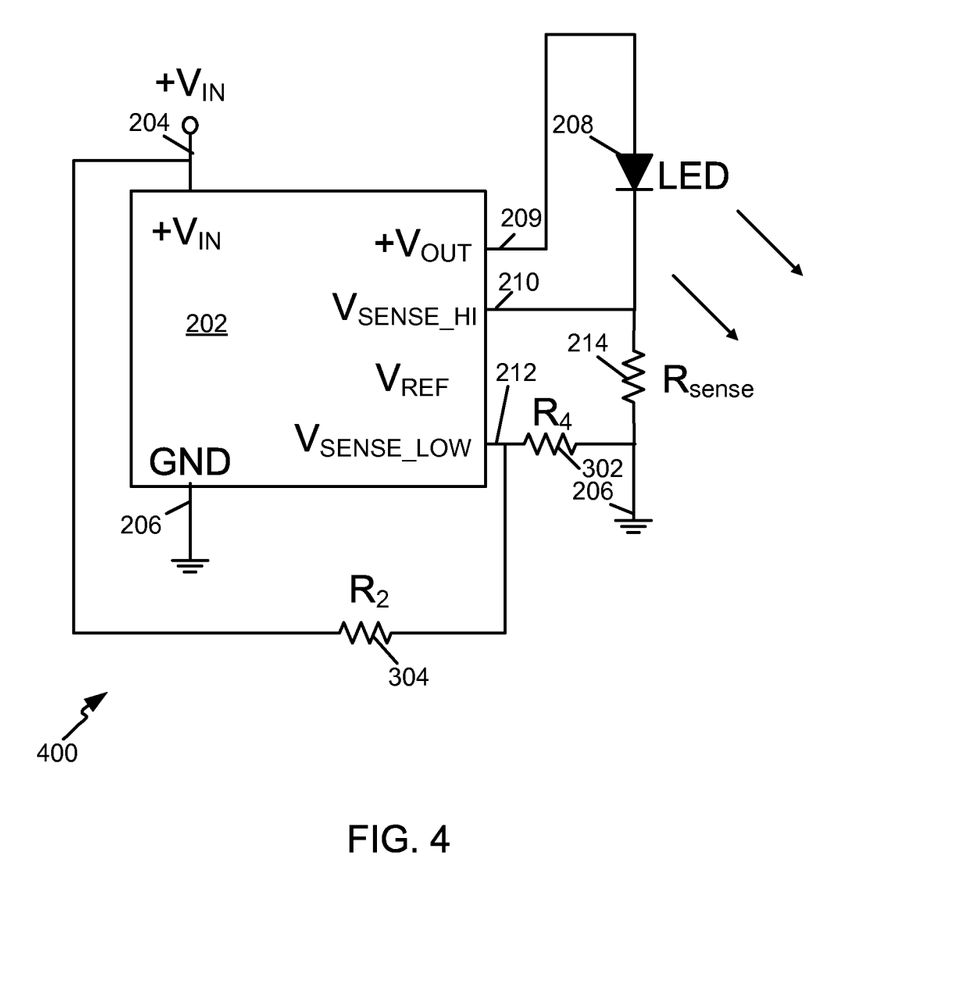
FIG. 4 is a schematic diagram of a possible LED drive circuit according to a second possible embodiment of the present disclosure.

Referring now to FIG. 4, a schematic diagram of a second LED drive circuit 400 is shown, according to a possible embodiment of the present disclosure. The LED drive circuit 400 generally is analogous to circuit 300; however, the light emitting diode 208 is connected between the output voltage 209 and the first voltage sense connection 210. In this arrangement, referred to herein as a "low side sense" arrangement (because the current sense resistor is on the low voltage side of the light emitting diode) the current across the light emitting diode can be derived similarly to that described above, and can be calculated from the following equation:

$$I_{led} = (V_{ref} + V_{in}(R4/(R2+R4)))/R_{sense}$$

In this arrangement, the current sensing occurs on the low-voltage side of the light emitting diode. The point between the current sense resistor 214 ($R_{sense}$) and the first current adjustment resistor 302 (R4) is connected to ground. This circuit arrangement provides analogous benefits to those described in connection with FIG. 3, above, but requires different selection of resistance values to arrive at the desired current across the light emitting diode 208 for the range of input voltages (to accomplish the target brightness and dimming desired in certain applications, e.g., medical scopes).

In certain embodiments of the current controller block 202, the output voltage 209 and first voltage sense connection 210 correspond to the same pin; in such arrangements, a "high-side sense" arrangement, such as that illustrated in FIG. 3 (or FIG. 5, below) is typically implemented (since in the "low-side sense" arrangement, the LED connects between these pins).

Figure 5:
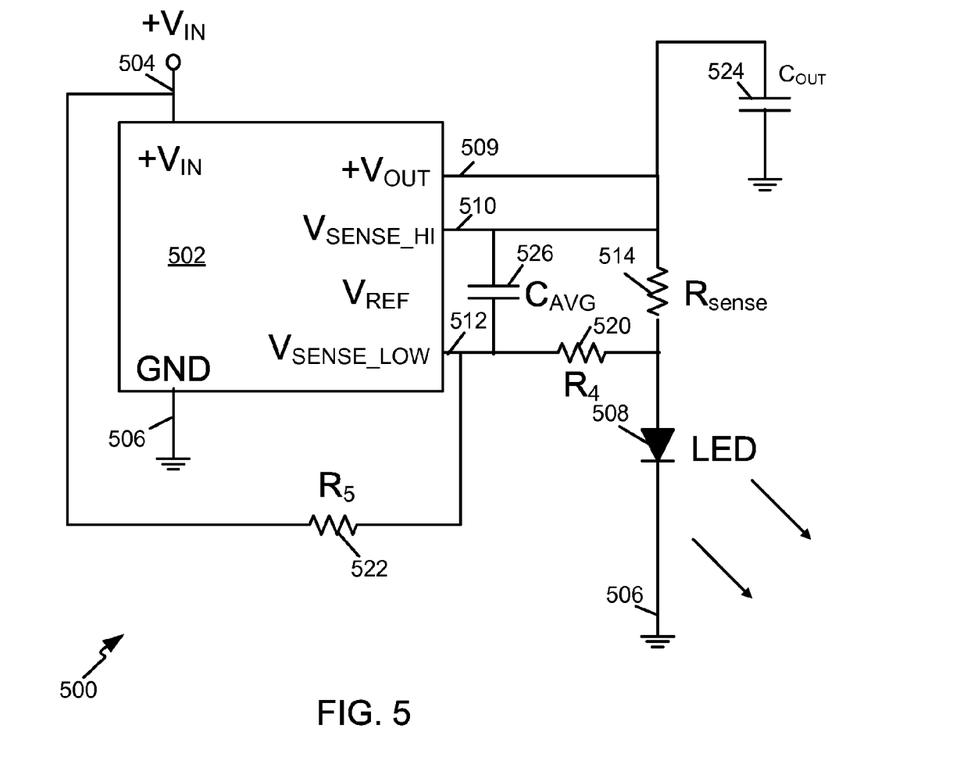
FIG. 5 is a schematic diagram of a possible LED drive circuit according to a third possible embodiment of the present disclosure.
Figure 6:
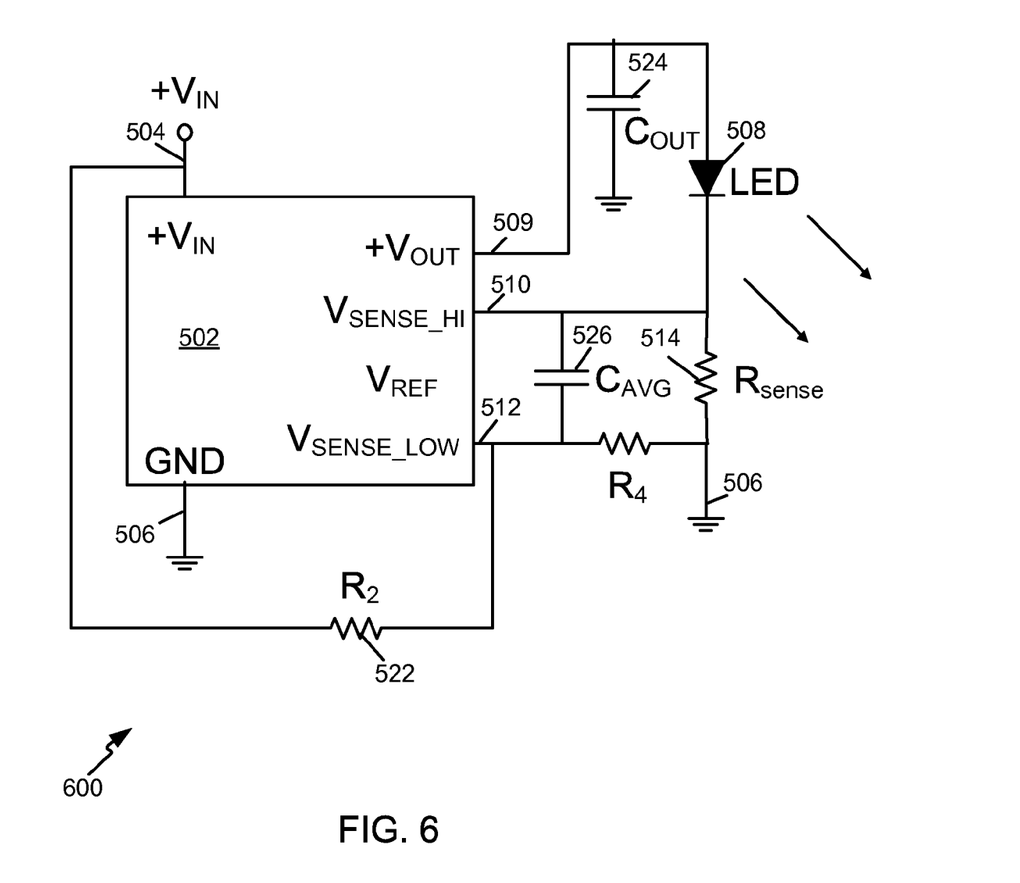
FIG. 6 is a schematic diagram of a possible LED drive circuit according to a fourth possible embodiment of the present disclosure.

Referring now to FIGS. 5-6, additional circuits are illustrated useable to provide dimming and control of a light emitting diode in a two input pin environment (input voltage and ground). The circuits described in FIGS. 5-6 are intended to describe additional features of circuits useable in such an environment and in which the current controller block includes a switching (rather than linear) controller.

FIG. 5 is a schematic diagram of a drive circuit 500 according to a further possible embodiment of the present disclosure. In this embodiment, a drive circuit 500 includes a switching current controller block 502 connected to an input voltage 504 and a ground 506. The switching current controller block 502 includes an output voltage 509, as well as a first voltage sense connection 510 and a second voltage sense connection 512. The first and second voltage sense connections are connected across a current sense resistor 514 ($R_{sense}$).

As with circuits 300 and 400, a voltage divider is formed from a first current adjustment resistor 520 and a second current adjustment resistor 522. The first current adjustment resistor 520 (R4) is connected between the current sense resistor 514 ($R_{sense}$) and the second voltage sense connection 512, and the second current adjustment resistor 522 (R2) is connected between the second voltage sense connection 512 and the input voltage 504. This causes the voltage at the second voltage sense connection 512 of the current controller block 502 to be affected by the difference between the input voltage and the voltage at the light emitting diode 508 in the manner described above. In the embodiment shown, a light emitting diode 508 is connected between a point between the current sense resistor and first current adjustment resistor 522 and a ground connection 506.

In addition to the voltage divider, circuit 500 includes capacitors 524 and 526, which generally provide a voltage averaging function for voltage across a light emitting diode 508. A first capacitor 524 ($C_{out}$) connects from the output voltage 509 and first voltage sense connection 510 to ground. A second capacitor 526 ($C_{avg}$) connects between the first and second voltage sense connections 510, 512, and, with current adjustment resistor 520 (R4), provides an averaging function for voltage across the current sense resistor 514 as the current controller block 502 switches. In the absence of the second capacitor 526 ($C_{avg}$), the first capacitor 524 ($C_{out}$) would be required to be very large to prevent a situation where the voltage across the current sense resistor 514 drops; in certain circumstances, such a voltage drop would cause a race condition in a switching current controller block 502. Inclusion of the second capacitor 526 ($C_{avg}$) and the first current adjustment resistor 520 (R4) vastly increases the time delay of capacitor discharge across the first and second voltage sense connections 510, 512, reducing the size of the first capacitor 524 ($C_{out}$) (or eliminating that capacitor entirely, in certain embodiments), and allowing the overall circuit to fit within a small package that would be able to be accommodated within a retrofit socket of a small-scale illumination device (e.g. a medical scope). In certain applications not requiring dimming, use of the second capacitor 526 ($C_{avg}$) provides this voltage stabilization benefit even in the absence of current adjustment resistor 522 (R5).

As can be seen from comparison of FIGS. 3 and 5, the circuit 500 of FIG. 5 represents a modification of the circuit 300 of FIG. 3 useable in certain switching circuits. FIG. 5 therefore illustrates a "high side sense" circuit, in which the current sense resistor 514 ($R_{sense}$) is on the high voltage side of the light emitting diode 508.

FIG. 6 illustrates a further possible embodiment of a switching circuit 600, representing a "low side sense" version of the circuit 500 of FIG. 6. In this embodiment, light emitting diode 508 is connected between the output voltage 509 and first voltage sense connection 510, and the low side of the current sense resistor 514 is connected to ground 506.

Figure 7:
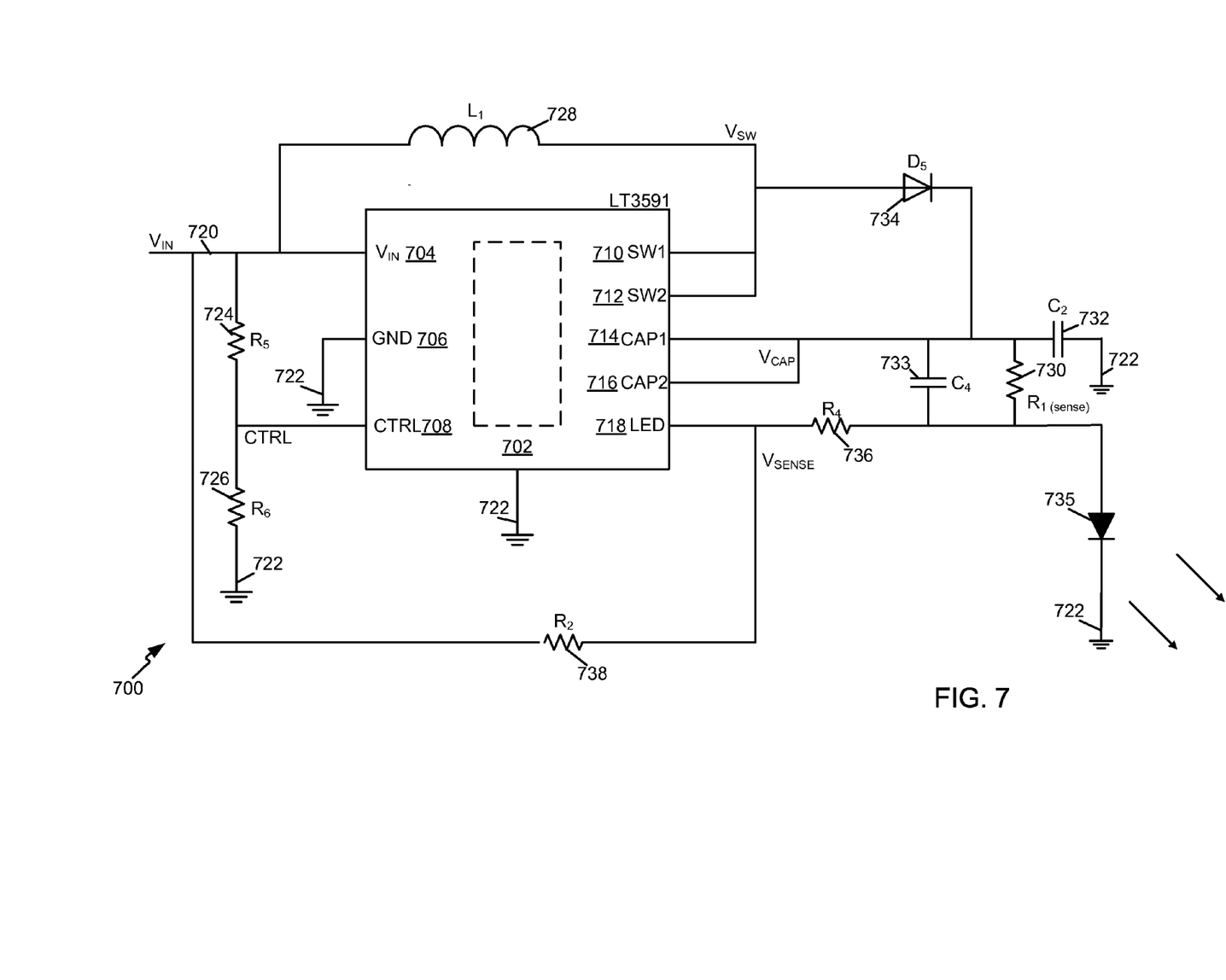
FIG. 7 is a detailed schematic diagram of a particular implementation of an LED drive circuit and installed LED, illustrating the features of the circuits of FIGS. 3 and 5, according to a possible embodiment of the present disclosure.

Referring now to FIG. 7, a detailed schematic diagram of a particular implementation of an LED drive circuit 700 is shown. The LED drive circuit 700 is, in the embodiment shown, a "high side sense" circuit, illustrating the features of the circuits of FIGS. 3 and 5, according to a possible embodiment of the present disclosure.

In the embodiment shown, the LED drive circuit includes a switching current control unit 702. In the embodiment shown, the switching current control unit 702 is an LT3591 LED driver manufactured by Linear Technology of Milpitas, Calif. This circuit is particularly designed for use in a "high side sense" circuit as illustrated; other current control units could be used as well in either high side sense or low side sense applications.

The switching current control unit 702 has a plurality of connections, including an input voltage connection 704, a ground connection 706, a dimming control connection 708, first and second switch connections 710, 712 (SW1, SW2), first and second high side voltage sense connections 714, 716 (CAP1, CAP2), and a low side voltage sense connection 718 (LED). In the embodiment shown, the input voltage connection 704 is connected to an input voltage 720 of the circuit. The ground connection 706 (and body connection, illustrated by grounded body 722) connect to the ground pin 724 available to the circuit 700.

Although the input voltage selected will vary depending upon the application to which the circuit 700 is directed, in certain embodiments, the input voltage can vary between approximately 1.8-1.9 volts to 4.0-4.1 volts. Other embodiments are possible as well.

The dimming control connection 708 is connected to the input voltage 720 via a voltage divider including first and second dimming control resistors 724, 726 (R5 and R6, respectively), such that the dimming control connection 708 operates at a constant fractional level of the input voltage 720. In certain embodiments, the dimming control connection 708 operates at approximately one third of the input voltage. In further embodiments, the dimming control connection 708 operates at approximately $^{36}/_{90}$ths of the input voltage 720. Other embodiments are possible as well.

The first and second switch connections 710, 712 (SW1, SW2) are interconnected, and feed back to the input voltage 720 via an inductor 728 (L1). The first and second high side voltage sense connections 714, 716 (CAP1, CAP2) are interconnected, and connected to (1) a high-voltage side of a current sense resistor 730 ($R_{sense}$), (2) a first output capacitor 732 (C2) (the opposite side of which is connected to ground 724), and (3) the forward side of a diode 734 (D5), the reverse side of which is connected to first and second switch connections 710, 712 (SW1, SW2). Additionally, a second output capacitor 733 (C4) connects between the first and second high side voltage sense connections 714, 716 (CAP1, CAP2) and the low side voltage sense connection 718 (LED), and operates as described above in FIG. 5 with respect to second capacitor 526 ($C_{avg}$). The low side voltage sense connection 718 (LED) also connects to the high side connection point for the light emitting diode 735 via a first current control resistor 736 (R4), and also connects to the input voltage via a second current control resistor 738 (R2).

The current sense resistor 730 ($R_{sense}$) connects between and a high-side connection point for a light emitting diode 734. In certain embodiments, the circuit 700 can include the light emitting diode 734; in other embodiments, the circuit 700 can include a socket arranged to receive the light emitting diode 734.

In the embodiment shown, the switching current control unit 702 has a reference voltage of approximately 0.2 V, meaning that the unit 702 maintains a constant 0.2 V difference between the first and second high side voltage sense connections 714, 716 (CAP1, CAP2) and the low side voltage sense connection 718 (LED).

The following table provides a listing of example circuit values, according to a possible embodiment of the circuit 700:

TABLE 1

Example Circuit Component Values

| | |
|---|---|
| current sense resistor 730 ($R_{sense}$) | 2.210 Ohms |
| first current control resistor 736 (R4) | 1 kOhm |
| second current control resistor 738 (R2) | 249 Ohms |
| first dimming control resistor 724 (R5) | 549 Ohms |
| second dimming control resistor 726 (R6) | 365 Ohms |
| first output capacitor 732 (C2) | 2.2 uF |
| second output capacitor 733 (C4) | 4.7 uF |
| inductor 728 (L1) | 22 uH |

It is understood that, although the above table provides example circuit values for components within the circuit 700 of FIG. 7, other values could be selected as well. The particular circuit values selected can depend, at least in part, on the number and characteristics of the LEDs used within the circuit 700. Additionally, in certain embodiments, the light emitting diode 735 can be implemented as an XPCWHT-L1-0000-B09E6 light emitting diode manufactured by Cree, Inc. of Durham, N.C. Additionally, the diode 734 (D5) can be implemented as a SBR07U20LPS-7 diode, manufactured by Diodes, Inc. of Dallas, Tex. Other possibilities exist as well.

Referring now to FIGS. 3-7 generally, it is recognized that the circuits of the present disclosure, including the voltage divider and optional capacitive components described above, can be used in retrofit applications to implement a light emitting diode arrangement where previous two-pin halogen or incandescent light sources were previously used. The circuits of the present application can be configured to maintain full functionality of the LEDs when installed, including dimming control and other features.

In general, it is noted that in the circuits described herein, the light emitting diodes used in the circuits will respond differently over time as they remain active. This is because the voltage drop across a light emitting diode drops as its temperature is raised (e.g., due to the light emitting diode remaining active and warming up for a few seconds). Referring back to the equation $I_{led} = (V_{ref} + (V_{in} - V_{led})(R4/(R2+R4)))/R_{sense}$, the circuits and systems of the present disclosure provide compensation for this additional effect by creating a greater LED current ($I_{led}$) when the voltage drop across the light emitting diode drops. This is because of the greater voltage difference between the voltage at the light emitting diode and the input voltage, which is assumed to remain constant (absent dimming adjustment). Other advantages exist as well, as are apparent above.

Furthermore, although the present current control circuit is discussed in the context of a medical scope, it is recognized that the circuit can be used in any of a variety of applications in which a light emitting diode is to be used in replacement for a halogen or incandescent bulb, particularly in applications where a two-lead connection is used, and dimming or other control functionality would be desirable. Example applications can include use in various illumination devices, such as a control panel display, a flashlight, other types of medical devices, or replacement parts (e.g., replacement bulb packages) therefor.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A drive circuit for a light emitting diode, the drive circuit comprising:
    an input voltage and a ground;
    a current control block including a voltage supply connection, a ground connection, a first voltage sense connection, and a second voltage sense connection, the voltage supply connection electrically connected to the input voltage and the ground connection connected to the ground, the current control block configured to maintain a constant voltage across the first and second voltage sense connections;
    a current sense resistor connected to the first voltage sense connection;
    a first current adjustment resistor connected between the current sense resistor and the second voltage sense connection; and
    a second current adjustment resistor connected between the second voltage sense connection and the input voltage, thereby forming a voltage divider at the second voltage sense connection, such that adjustment of the input voltage proportionally changes a voltage across the light emitting diode at a constant current.

2. The drive circuit of claim 1, wherein a light emitting diode can be connected from a point between the current sense resistor and the first current adjustment resistor to the ground.

3. The drive circuit of claim 2, wherein current at a light emitting diode is at least partially controlled by the input voltage.

4. The drive circuit of claim 1, wherein the first current adjustment resistor has a resistance greater than a resistance of the current sense resistor.

5. The drive circuit of claim 1, wherein the current control block further includes an output voltage connection, and wherein a light emitting diode can be connected between the output voltage connection and the first voltage sense connection.

6. The drive circuit of claim 1, wherein the second current adjustment resistor has a resistance greater than a resistance of the current sense resistor.

7. The drive circuit of claim 1, wherein a dimming control is set by a ratio between the first and second current adjustment resistors.

8. The drive circuit of claim 1, wherein a plurality of light emitting diodes can be connected from a point between the current sense resistor and the first current adjustment resistor to the ground.

9. The drive circuit of claim 1, wherein the current control block comprises a switching controller.

10. The drive circuit of claim 9, further comprising a capacitor connected between the first and second voltage sense connections, the capacitor selected to provide an approximately constant voltage across the first and second voltage sense connections.

11. The drive circuit of claim 10, wherein the approximately constant voltage reflects an average current passing through a light emitting diode connected from a point between the current sense resistor and the first current adjustment resistor to the ground.

12. A replacement light emitting diode package useable in an illumination device, the replacement light emitting diode package comprising:
    an input voltage and a ground;
    a current control block including a voltage supply connection, a ground connection, a first voltage sense connection, and a second voltage sense connection, the voltage supply connection electrically connected to the input voltage and the ground connection connected to the ground; the current control block configured to maintain a constant voltage across the first and second voltage sense connections;
    a current sense resistor connected to the first voltage sense connection;
    a first current adjustment resistor connected between the current sense resistor and the second voltage sense connection;
    a second current adjustment resistor connected between the second voltage sense connection and the input voltage; and
    a light emitting diode connected from a point between the current sense resistor and the first current adjustment resistor to the ground, such that adjustment of the input voltage proportionally changes a voltage across the light emitting diode at a constant current.

13. The replacement light emitting diode package of claim 12, wherein the illumination device comprises a medical scope.

14. The replacement light emitting diode package of claim 12, wherein the illumination device comprises an orifice scope.

15. The replacement light emitting diode package of claim 12, wherein current at a light emitting diode is controlled by the input voltage.

16. The replacement light emitting diode package of claim 12, wherein the illumination device is selected from the group consisting of:
    a control panel display;
    a medical device; and
    a flashlight.

17. A medical scope comprising:
    a voltage source electrically connected to a socket, the socket comprising a voltage pin and a ground pin;
    a light emitting diode package sized to fit in the socket, the light emitting diode package including:
        a current control block including a voltage supply connection, a ground connection, a first voltage sense connection, and a second voltage sense connection, the voltage supply connection electrically connected to the voltage pin of the voltage source and the ground connection connected to the ground pin, the current control block configured to maintain a constant voltage across the first and second voltage sense connections;
a current sense resistor connected to the first voltage sense connection;
a first current adjustment resistor connected between the current sense resistor and the second voltage sense connection;
a second current adjustment resistor connected between the second voltage sense connection and the input voltage; and
a light emitting diode connected from a point between the current sense resistor and the first current adjustment resistor to the ground, such that adjustment of the input voltage proportionally changes a voltage across the light emitting diode at a constant current.

18. The medical scope of claim 17, wherein current at a light emitting diode is at least partially controlled by the input voltage.

19. The medical scope of claim 17, wherein the current control block comprises a switching controller.

20. The medical scope of claim 19, wherein the light emitting diode package includes a capacitor connected between the first and second voltage sense connections, provide an approximately constant voltage across the first and second voltage sense connections.

21. The medical scope of claim 17, wherein a dimming control is set by a ratio between the first and second current adjustment resistors.

22. A drive circuit for a light emitting diode, the drive circuit comprising:
an input voltage and a ground;
a current control block including a voltage supply connection, a ground connection, a first voltage sense connection, and a second voltage sense connection, the voltage supply connection electrically connected to the input voltage and the ground connection connected to the ground, the current control block configured to maintain a constant voltage across the first and second voltage sense connections;
a current sense resistor connected to the first voltage sense connection;
a first current adjustment resistor connected between the current sense resistor and the second voltage sense connection;
a second current adjustment resistor connected between the second voltage sense connection and the input voltage; and
a capacitor connected between the first and second voltage sense connections, the capacitor selected to provide an approximately constant voltage across the first and second voltage sense connections, such that adjustment of the input voltage proportionally changes a voltage across the light emitting diode at a constant current.

* * * * *